United States Patent [19]

Averback

[11] Patent Number: 4,816,416
[45] Date of Patent: Mar. 28, 1989

[54] MICROSPHERIC BODIES FOR USE IN SCREENING THERAPIES FOR AZHEIMER'S DISEASE AND RELATED CONDITIONS

[76] Inventor: Paul Averback, 5265 Westmore Ave., Montreal, Quebec, Canada

[21] Appl. No.: 21,242

[22] Filed: Mar. 3, 1987

Related U.S. Application Data

[63] Continuation-in-part of Ser. No. 901,007, Aug. 27, 1986, abandoned.

[51] Int. Cl.$^4$ ............................................ G01N 21/78
[52] U.S. Cl. .................................... 436/166; 128/630; 424/7.1; 424/9; 424/95; 436/2; 436/164; 436/183; 436/811
[58] Field of Search ...................... 436/2, 63, 164, 177, 436/178, 183, 811, 166; 435/5; 128/1 R, 630, 749; 424/7.1, 9, 95

[56] References Cited

U.S. PATENT DOCUMENTS

| | | | |
|---|---|---|---|
| 4,267,271 | 5/1981 | Roberts | 436/804 X |
| 4,316,895 | 2/1982 | Kimball et al. | 530/845 X |
| 4,448,779 | 5/1984 | Blanchard et al. | 514/301 |
| 4,550,109 | 10/1985 | Folkers et al. | 514/249 |
| 4,578,394 | 3/1986 | Allen et al. | 514/332 |
| 4,605,652 | 8/1986 | Welstead | 514/214 |
| 4,666,829 | 5/1987 | Glenner et al. | 436/63 X |

OTHER PUBLICATIONS

Averback, Medline abstract of Acta Neuropathol., vol. 61, No. 2, pp. 148–152, 1983.
Averback, "Immunofluorescent Staining of Dense Microspheres in Human Brain," *Arch Pathol Lab Med.*, vol. 106:394 (1982).
Averback, "The Dense Microsphere: A Newly Delineated Origin of the Senile Plague in Human Brain," *The Canadian Journal of Neurological Sciences*, 284 (May 1982).
Averback, "Ultrastructural Studies of the Origin and Growth of Dense Micro-Spheres in Normal Human Brain," *The Canadian Journal of Neurological Sciences*, 290 (May 1982).
Averback, "Morphometric and Anatomical Correlation of Dense Microsphere and Senile Plague Formation in Alzheimer's Disease," *Lejournal Canadien Des Sciences Neurologiques*, 283 (May 1982).
Averback, "Quantitative Correlations of Dense Microspheres and Senile Plagues in Alzheimer Disease," *Neurology*, 32(2) (May 1982).
Averback, "Population, Distribution, and Growth of Dense Miceospheres in the Human," *Federation Proceedings*, vol. 41, (Mar. 1982).

*Primary Examiner*—Barry S. Richman
*Assistant Examiner*—Robert J. Hill, Jr.
*Attorney, Agent, or Firm*—Foley & Lardner Schwartz Jeffery, Schwaab, Mack, Blumenthal & Evans

[57] ABSTRACT

Dense microspheres extracted and purified to homogeneity from whole brains and used in in vitro and in vivo screening tests for the detection of therapies effective in impeding amyloid formation and disease progression in human brain in Alzheimer's disease and related conditions.

7 Claims, 1 Drawing Sheet

MICROSPHERIC BODIES FOR USE IN SCREENING THERAPIES FOR AZHEIMER'S DISEASE AND RELATED CONDITIONS

This application is a continuation-in-part of application Ser. No. 901,007 (filed Aug. 27, 1986), now abandoned.

BACKGROUND OF THE INVENTION

This invention relates to microspheric bodies derived from brain cells. This invention also relates to the purification of these microspheric bodies to homogeneity and to their use in screening proposed therapeutic measures for effectiveness in impeding amyloid formation and disease progression in human brain affected by Alzheimer's disease and related conditions. More specifically, the present invention is directed to dense microspheres obtained in purified form from brain cells, to the preparing of the dense microspheres in a usable form, and to methods for using them in the identification of therapies for treating Alzheimer's disease and related conditions associated with the formation of amyloid fibrils in the brain.

Alzheimer's disease is an incurable brain disease affecting middle aged and elderly people throughout the world. According to most recent estimates, it is the 4th or 5th leading cause of death among North Americans, and is responsible for inestimable personal and social tragedy, loss of productivity, and custodial burden to society. There is presently no widely-accepted effective treatment for Alzheimer's disease.

The principal symptom (manifestation) of Alzheimer's disease is the loss of higher mental faculties, typified by the loss of memory and behavior referred to as "dementia." Dementia is a symptom complex or syndrome which can be seen in many brain diseases other than Alzheimer's disease, such as stroke, encephalitis and metabolic diseases. Since memory loss and dementia are relatively nonspecific symptoms, a certain and specific definition of Alzheimer's disease is based on the characteristic microscopic state of the brain, described initially by Marinesco, Alzheimer and others [see Alzheimer, A., *Allgemeine Zeitschrift fur Psychiatrie* 64: 146–148, (1907); Marinesco, G., *Comptes Rendus des Seances de la Socieete de Biologie et ses Filiales* 70: 606–608 (1911)].

The particular microscopic feature that is a universally accepted indicator of Alzheimer's disease, and that separates Alzheimer's disease from other causes of dementia, is the accumulation of large numbers of brain lesions referred to as senile plaques and neurofibrillary tangles. These lesions (microscopical areas of abnormal brain tissue), when found in suitable quantity in a brain sample, are the definitive criteria for the diagnosis of Alzheimer's disease.

The clinical diagnosis of Alzheimer's disease is often a difficult and imperfect task which generally relies initially on ruling out other treatable or clinically definable causes of dementia. In the appropriate clinical context, if the latter causes cannot be proven, Alzheimer's disease is often diagnosed antemortem, by exclusion, as the most probable diagnosis. Many indirect methods of diagnosis at present are being proposed and tested [see Conference Report, Khachaturian, *Z. Arch. Neurol.* 42: 1097–105 (1985)]; but the only certain and acceptable method for diagnosing Alzheimer's disease is by tissue microscopic histological study of a brain biopsy or necropsy sample, in which the above-mentioned sine qua non lesions are recognized by a certified specialist with adequate expertise.

Senile plaques in large quantities are essentially found only in the Alzheimer group of diseases; in contrast, neurofibrillary tangles are nonspecific, found in at least ten other neurological diseases [see Corsellis, J.A.N., GREENFIELD's EUROPATHOLOGY 951-1025 (4th ed. 1984) (Edward Arnold, London)]. Individual senile plaques have roughly 1000X the volume of individual neurofibrillary tangles. True measurements of total brain senile plaque and neurofibrillary tangle content are not available, but on the above basis it is likely that the volume of abnormal brain tissue occupied by senile plaques is many hundreds of times that of neurofibrillary tangles. The essential feature of the senile plaque is the presence of amyloid fibrils ("amyloid"), which are a congophilic red-green birefringent microfibrillar material (Corsellis, loc. cit.).

The utilization of materials found in human brain (normal or affected by Alzheimer's disease) that are not initially amyloid and transforming them into amyloid has not been documented. Thus an experimental system, derived from human materials, characterized by the sine qua non feature of human Alzheimer's disease has not been documented. A fundamental approach to treating a disease is to reproduce the disease experimentally in a nonhuman context and to test potential treatments for their effect on the experimental disease. Because the presence of amyloid provides a definitive indication of senile-plaque formation, most specialists agree that reproduction of amyloid fibrils experimentally from precursor materials which are extracted, activated, or otherwise derived from the human brain would constitute the best available evidence linking an agent or precursor to the progression of Alzheimer's disease. Despite much investigation into this question during the past fifty years, the fundamental step of reproducing amyloid experimentally from materials derived solely from human brain tissue has not been documented.

A microscopic structure referred to as the dense microsphere is known to exist in normal brain and in brain affected by Alzheimer's disease brain (Averback, *Acta Neuropathol.* 61: 148–52 (1983); results confirmed by Hara, M., *J. Neuropath. Exp. Neurol.* 1986). Some specialists believe that dense microspheres ("DMS") may be connected somehow to the formation of amyloid senile plaque, but this hypothesis has not been proven. Evidence for the existence of DMS comes from microscopic histological section studies of fixed whole brain tissue, where the dense microspheres are observed as randomly dispersed, highly infrequent structures occupying an estimated $10^{-9}$ or less of total brain volume, at a unit frequency roughly estimated at $10^{-16}$ or less, relative to other definable brain structures such as mitochondria. But the extraction, purification and characterization of isolated samples, and the use of tangible DMS material to any advantage, have not been documented. Without these developments, DMS are structures of unproven function, unknown significance or usefulness, are not in tangible form and are not readily available.

SUMMARY OF THE INVENTION

It is therefore an object of the present invention to provide dense microspheres derived from brain cells in essentially homogeneous, purified form.

It is another object of the present invention to provide a method for screening therapies for utility in impeding amyloid formation and disease progression in human brains affected by Alzheimer's disease and related conditions.

In accomplishing the foregoing objects, there has been provided, in accordance with one aspect of the present invention, a composition of matter consisting essentially of dense microspheres derived from mammalian brain tissue, which bodies provide, when disrupted, material that displays congophilic birefringence.

In accordance with another aspect of the present invention, a method has been provided for screening for the ability to impede amyloid formation, comprising the steps of (i) disrupting dense microspheres derived from mammalian brain tissue to form a material that is stainable with Congo Red stain; (ii) contacting the material with Congo Red stain and then (iii) subjecting the material to optical-microscopic examination to detect any congophilic birefringence. In a preferred embodiment, the method of the present invention further comprises the step, prior to step (i), of contacting the dense microspheres with a pharmacological agent, in order to ascertain the amyloid formation-impeding activity of that agent.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

It has now been found to be most likely that, as a result of some presently uncontrollable mechanism in the brain cells of certain living beings, DMS is disrupted to cause senile-plaque amyloid formation and, thereby, serious damage to the brain in the form of the lesions that are characteristic of Alzheimer's disease. The connection between DMS disruption and amyloid formation is established by the fact that disrupted DMS treated with Congo Red stain display a red-green congophilic birefringence identical to that found diagnostically in Alzheimer's disease senile-plaque amyloid.

In other words, the most significant aspect of the brain damage accepted as characterizing Alzheimer's disease can, for the first and only known time, be induced and reproduced (according to established and conventional criteria) from and in material derived, pursuant to the present invention, exclusively from undamaged human brain samples.

The microspheric bodies employed in the present invention are derived from mammalian brain tissue and are characterized, in essentially homogeneous purified form, by a range of diameters from about 0.1 to about 15 microns, by an outer membrane that surrounds proteinaceous matter, and by certain stainability properties. For example, the microspheric bodies according to the present invention are homogeneously electron-dense when stained with osmium and lead, and can be visualized by thin-section electron microscopy; under optical microscopic examination, they appear eosinophilic and phloxinophilic, and are nonbirefringent when stained with Congo Red. When the microspheric bodies of the present invention are disrupted, a material is produced that displays congophilic birefringence; that is, when stained with Congo Red the material becomes optically anisotropic to the extent of splitting an incident light wave into two waves with mutually perpendicular vibration directions.

Figure 1:
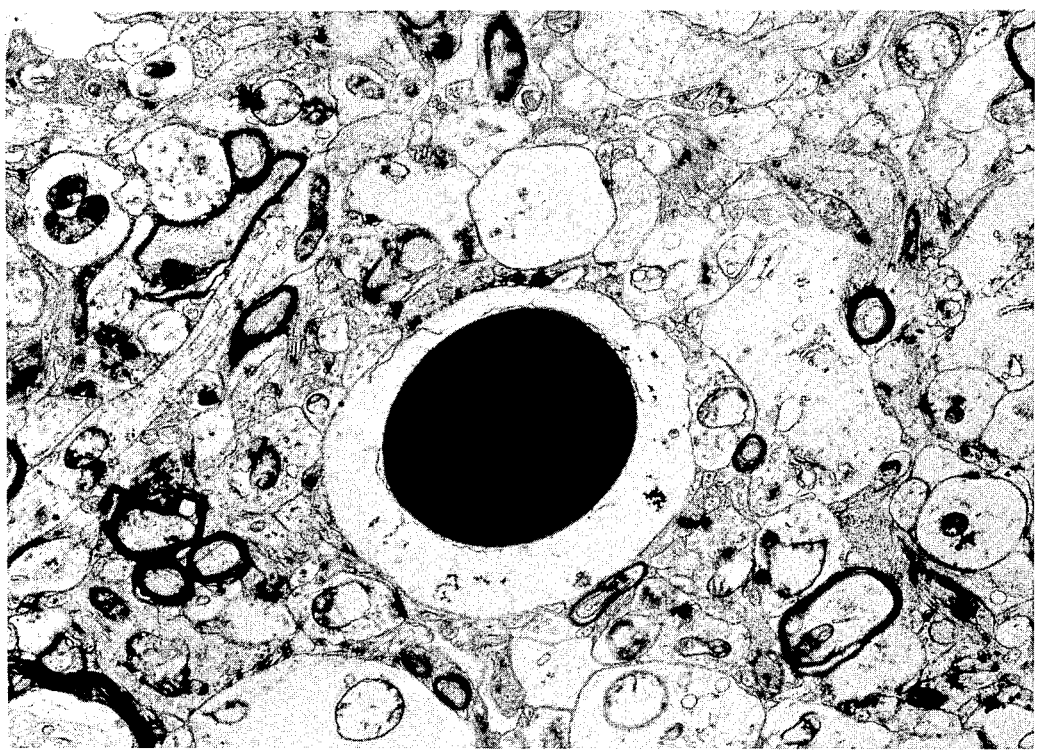
FIG. 1 is a micrographic representation of a DMS.
Figure 2:
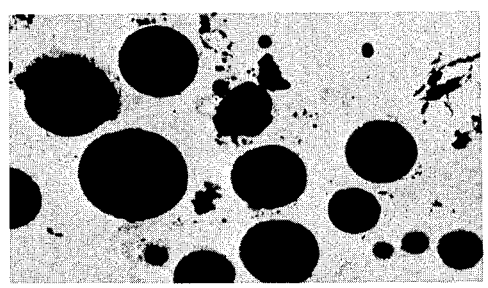
FIG. 2 is another micrographic representation showing DMS in homogeneous form.

As shown in FIG. 1, DMS are spherical, membrane-bounded, intracellular structures, about 0.1 to 15 microns in diameter, that are found in human and other mammalian brains. Homogeneous structures of DMS in purified from can be derived by extraction to give tangible samples of homogeneous globular bodies.

The following procedure can be followed to extract DMS from brain tissue;

(1) Whole brain is removed from the skull postmortem, by use of standard postmortem techniques for humans or animals. The best results are obtained if the organism has been in circulatory arrest for less than six hours at the time of brain removal and if the body has been refrigerated as early as possible postmortem. DMS are still extractable at postmortem intervals greater than six hours and are still extractable if body cooling has been delayed or absent, but these two factors will usually greatly decrease the overall average yield of DMS per individual brain. In addition to the effects of post-circulatory arrest interval and temperature on DMS yield, there is considerable individual variation in DMS content per brain, and also individual variation in DMS extractability, which may be related to agonal metabolic state, overall disease status or other factors. All of the factors which determine total DMS yield per brain can have an impact on DMS extraction, since the volume of purified sample of homogeneous DMS will decrease proportionally to any reduction in percentage extractability; such a decrease may be sufficient to hinder accurate recognition during the extraction procedure. Furthermore, the screening of putative Alzheimer's disease therapies and the characterization of isolated samples of DMS, in accordance with the present invention, are rendered correspondingly more difficult and costly, and ultimately may be impossible at critically small volumes of DMS.

(2) By means of clean instruments, the freshly removed brain is immediately dissected. Dissection is optimally performed in a cold room at 10° C. By means of careful, but rapid, sharp and blunt dissection, the internal capsules, corona radiata, centra semi-ovale, brainstem, cerrebellum, lepto and pachymeninges, arachnoid granulations, choroid plexi, and blood vessels are separated and discarded, and the remaining mass of brain is rapidly used for the subsequent steps. (Standard blocks for microscopic study can be removed at this stage and stored separately in histological fixative.) The dissected brain mass ("DBM") is optimally utilized immediately after dissection. It may also be stored frozen at temperatures of −10° C. to −70° C, but this decreases the overall average yield of DMS per individual brain.

(3) The extraction of DSM material from DBM can be carried out by a combination of centrifugation steps. In an exemplary extraction, DBM mechanically homogenized in a 2:1 volume of 0.5M TRIS-HCL buffer (pH 7.5) is subjected to centrifugation at about 200 rpm for some 10 minutes. (All manipulations are carried out at around 4° C.) The sediment thus obtained ("Sediment I") is separated across a sucrose gradient (1.589M, or 45%; 1.895M, or 52%; 2.3895M, or 62.5%) via centrifugation at 26,000 rpm for 30 minutes. It has been found that the material that settles at the interface between 1.895M and 2.1015M (56.7% sucrose) is the DMS-containing fraction, as may be confirmed by microscopic examination, with eosin staining, of the fraction.

The DMS-containing fraction obtained from Sediment I consists essentially of the dense microspheres described above, and can be used in a screening method according to the present invention. It is preferable, however, for the fraction to be subjected to additional manipulations in order to enrich the DMS concentration. To this end, it has proved useful, for example, to wash the DMS-containing fraction in buffer—the above-mentioned homogenization buffer is suitable for this purpose—nd to spin the resulting mixture again (10,000 rpm for 7 minutes) to obtain DMS-enriched sediment ("Sediment II").

As with Sediment I, Sediment II can be run through a density gradient to enrich further the yield of DMS. It has been discovered that the carbohydrate Percoll® (Pharmacia) is particularly useful in this context. A commercially available formulation of 80% Percoll (1.13 g/ml) in 0.15M NaCl provides a isoosmolar gradient to which Sediment II can be subjected (30,000 rpm for 15 minutes); successive samples, say, on the order of 0.25 to 1 cc each, can then be taken along the length of the gradient and the DMS-enriched fractions isolated. After these fractions are washed again in buffer, they can be spun down once again (15,000 rpm for 10 minutes) to obtain a sediment ("Sediment III") that is substantially pure DMS.

The DMS materials obtained as described above can be used, pursuant to the present invention, in screening Alzheimer's disease therapies. More specifically, a DMS material within the present invention can be employed to ascertain effectiveness, on the part of an active agent or treatment comprising a putative Alzheimer's therapy, in preventing the red-to-green congophilic birefringence that accompanies the formation of amyloid when DMS are disrupted. By whatever means DMS are disrupted in control samples, a proposed therapy can be screened by virtue of its ability to retard or preclude amyloid formation under test conditions.

For example, in vitro DMS disruption on an appropriate viewing surface, such as a glass or plastic slide (see Test 1 below), can be accomplished by mechanical means; by the action of an enzyme treatment, as in a 10% trypsin or pepsin solution, or other chemical exposure, as to a 10% guanine solution; or by exposing DMS material to extreme pH values (at room temperature, pH2 or pH10) or temperatures (e.g., 100° C. for one hour). Disruption of DMS can also be effected by injecting DMS material of the present invention into an isolated tissue sample (see Test 2); brain slices are preferred for this purpose, but liver, pancreas and other organs are also acceptable sources for tissue samples.

Alternatively, DMS can be disrupted in vivo, by injecting the purified DMS material of the present invention into a suitable laboratory animal. Since simple injection of DMS onto a glass slide does not result in amyloid formation, it is understood that DMS disruption (and production of amyloid) in vivo, as reported in Example 2 below, occurs in the extracellular spaces of the injected tissue. Although brain sites for injection are preferred, injection sites elsewhere in a test animal's body, such as in skin and in muscle, are suitable for determining the ability of a proposed active agent or treatment step to hinder the resulting formation of amyloid.

The following test paradigms illustrate various ways in which DMS material, as described above, can be used according to the present invention to screen potential Alzheimer therapies.

TEST 1. In vitro disruption of DMS on a glass slide.

Homogeneous DMS preparations are placed by droplet on a clean dry glass slide. The volume and number of DMS used is optional but is recommended to be at least several thousand to facilitate interpretation (see Example 1 below). Larger samples are more costly but are easier and more unequivocal to examine. The DMS are mechanically disrupted using a stainless steel spatula scraping and pressing the DMS against a glass slide in repetitive manual back and forth motions for one minute.

The slide is allowed to air dry. A few drops of Congo Red stain are then added to the dried slide and gently passed over the dried disrupted DMS for 30 seconds and the stain is then drained off the slide onto tissue paper or filter paper. The slide is then examined in the light microscope, the latter fitted with crossed polarizing lenses to assess red-green congophilic birefringence. The result is an unequivocal red-to-green ("apple green") birefringence similar to the red-to-apple green birefringence found in the senile-plaque amyloid of Alzheimer patients, and in quantities proportional to the volume of DMS applied to the slide initially. All other reactions, staining results, or quantitatively insignificant results are considered negative in the absence of the characteristic color change-positive staining result, in quantity proportional to the volume of DMS applied, which indicates that disrupted DMS are of the nature of senile-plaque amyloid.

For test purposes, a corresponding DMS sample is contacted with a possible pharmacological agent, and the DMS disruption/staining procedure as described above is repeated. Many variations are possible, e.g., the active agent may be applied to the DMS in solution, before application to the slide, or to the DMS on the slide. In any event, an observation that the agent prevents development of the red-green birefringence in the above-described negative control slide (no agent present) is a clear indication that the active agent should be tested further for efficacy against Alzheimer's disease.

As a positive control, the test slide can also be compared to a slide upon which DMS were disrupted after contact with a 1% aqueous solution of diphenyl disazo binaphthionic acid, $[C_6H_4N_2C_{10}H_5[NH_2]SO_2ONa]_2$; the compound, Congo Red, is described by Graves & Kickham, *New England J. Med.* 214: 782-83 (1936), and Wallace, *The Lancet* (Feb. 20, 1932), at 391-393, an has been found to block amyloid formation in the present invention.

TEST 2. In vitro disruption of DMS in a human brain slice.

Human brain postmortem samples of histological block size (block size is elective; usually 1–tcm ×1–5 cm×1–3mm) are removed, by sterile techniques, with the aid of sterile gloves, scalpel and forceps, and then are placed in sterile empty plastic containers, such as a Petri dish before extracted DMS are injected into each brain sample at room temperature. After one hour incubation at room temperature, the brain samples are immersed in situ in histological fixative and processed for histology by techniques that are standard for optical microscopy. Controls, size of inoculum, preparations of slides and interpretation of results are covered under discussion of in vivo Test 3 below.

TEST 3. In vivo disruption of DMS by injection into live tissue.

Laboratory rodents are anesthetized and their brains immobilized by routine methods and injections of purified DMS are made into superficial cerebral cortex regions through sterile needles inserted through the skull and meninges. (Sham control injections of DMS negative material can be put into either the contralateral cortex or into separate animals.) The method of anesthesia, type of craniotomy, site of injections in the brain parenchyma, size of needle and syringe or other vehicle, wound closure technique, and numbers of animals used are not crucial to the test and will vary depending on the animal used. Thus, a small mouse may not need a skull flap whereas a larger mammal may need a burr hole; size of needles or vehicles may vary with animal brain size, etc. (see Example 1). The size of injection is elective: smaller injections are more difficult and costly to trace histologically (see below), but larger injections are more costly in terms of numbers of DMS used. (A sample protocol is detailed in Example 1.) The animal is painlessly sacrificed 0.5 hours or more after injection. The exact time of sacrifice is elective: generally 1–24 hours is preferable but the DMS transformation will persist and can be recognized at many time intervals. After sacrifice the brain is removed by standard methods and immersion fixed in histological fixative. Perfusion fixation is not recommended because perfusion pressures will usually disrupt the injection cavity and render the results inaccessible. According to standard methods, the brain is fixed in toto for several days (correspondingly longer for larger animal brains), sliced, embedded, cut, mounted and stained for histological study. A dissecting microscope is used to locate the injection site and accurately place it in the block, and sections are carefully inspected during microtomy to ensure that the injection site is in the section and not discarded during trimming. the mounted slides are stained with Congo Red according to the standard method. The sections are examined with the optical microscope fitted with polarizing lenses as above and assessed as described above with regard to the in vitro test.

The use of positive and negative controls, and the testing of putative active agents, are carried out in a manner analogous to that followed the in vitro tests described above, with further variations possible by virtue of the fact that test compounds can be are tested in vivo via injection, ingestion and/or other possible routes, before, after or during the introduction of DMS, with or without the DMS. In addition, therapeutic strategies other than those based on the action of a pharmacological agent can be studied in whole animals.

By means of the above tests, nontoxic compounds suitable for clinical testing in human beings can be found, pursuant to the present invention, that block the transformation of dense microspheres into amyloid. Because it is immunogenic in standard laboratory animals, the DMS material of the present invention can also be used to produce polyclonal and monoclonal antibodies against dense microspheres. These antibodies, in turn, can be employed in ELISA-type assays, see, e.g., VOLLER et al, THE ENZYME LINKED IMMUNOSORBENT ASSAY (ELISA) (Dynatech Laboratories 1979), and other immunological tests, such as radioimmunoassays, for detecting DMS in biological samples. Via conventional techniques, as described, for example, by Kennet et al, *Curr. Top. Microbiol. Immunol.* 81: 77–91 (1978), anti-DMS antibodies can be produced using the DMS material of the present invention and then "tagged" with a radionuclide, a colorimetric agent or a fluorescent marker. The tagged antibodies can be used in diagnostic tests to detect the presence of the dense microspheres with which the antibodies react, rendering the microspheres visualizable.

Other details of the present invention are further described by reference to the following illustrative examples.

EXAMPLE 1

Approximately 80,000 homogeneously extracted DMS were placed in a droplet from a Pasteur pipette onto a glass slide, and the droplet was air dried. The DMS adhered to the glass slide. Acetylcholine (20 mM) in physiological saline was added in a droplet, as a possible test compound, to DMS. The DMS were mechanically disrupted, in the presence of the test compound, as described above and then were allowed to air dry. A control slide was treated exactly in the same manner, except that the test compound was not added. Congo Red stain was added, and the reaction products were examined, as previously described. Under optical-microscopic examination with a polarizing lens, both slides showed abundant reddish stained material, respectively, in quantities of the order of magnitude as in the initial DMS droplet quantity. The reddish material was observed to turn a brilliant apple green during rotation of the polarizing lens. Rotation of the polarizing lenses back and forth demonstrated unequivocal and abundant red-to-green and green-to-red birefringence which persisted indefinitely. That both slides showed these indistinguishable results meant that acetylcholine had tested negative, i.e., had showed no useful activity in this test.

EXAMPLE 2

Four male Wistar rats of 3 months age were anesthetized by ether inhalation. Their heads are immobilized by means of a stereotactic head brace. Bilateral parieto-occipital scalp incisions (1 cm) were made with a sterile scalpel blade. Bilateral parieto-occipital 0.5 mm burr holes are made with a 0.5 mm drill. In two rats 400,000 human DMS are injected on one side through the burr hole from a sterile 1 cc syringe fitted with a sterile 22 gauge needle. The injection was made into the cerebral cortex to a depth of a few mm so that the injection was within the parenchyma, not on the surface and not in the ventricles. On the contralateral side, 100 μL of homogenized whole human brain were injected. In two rats, the DMS as above were injected on one side, while on the contralateral side 100 μL of sterile physiological saline were injected. One rat from each group had been premedicated with a test compound; the other rat had not been treated.

After injection, a sterile suture was placed through the scalp incision to cover the wound, and the animals are observed for one hour. After one hour the animals were painlessly sacrificed by ether inhalation and $CO_2$ insufflation. The brains were removed and processed, and the results interpreted, as described above, with the result that the test compound was found to be effective in preventing formation of amyloid senile plaque.

What is claimed is:

1. A composition of matter consisting essentially of a suspension of dense microspheres in a liquid carrier, said dense microspheres in said liquid carrier being derived from mammalian brain tissue and providing, when disrupted, material that displays congophilic birefringence.

2. A composition according to claim 1, wherein said microspheres are present in said suspension in essentially homogeneous, purified form.

3. A composition according to claim 1, wherein said liquid carrier is a buffer solution.

4. A composition that is the product of a process comprising the steps of (A) subjecting homogenized mammalian brain to a first centrifugation, at about 200 rpm for about 10 minutes, to obtain a sediment; (B) separating said sediment across a sucrose gradient via a second centrifugation at about 26,000 rpm for about 30 minutes, said sucrose gradient comprising a variation in sucrose concentration between at least a first level of about 52% sucrose content and a second level of about 56.7% sucrose content and further comprising an interface between said first level and said second level; and (C) isolating material that settles at the interface between said first level and said second level of said gradient, said material containing dense microspheres.

5. A composition that is the product of a process comprising the steps of (A) subjecting homogenized mammalian brain to a first centrifugation, at about 200 rpm for about 10 minutes, to obtain a sediment; (B) separating said sediment across a sucrose gradient via a second centrifugation at about 26,000 rpm for about 30 minutes, said sucrose gradient comprising a variation in sucrose concentration between at least a first level of about 52% sucrose content and a second level of about 56.7% sucrose content and further comprising an interface between said first level and said second level; (C) isolating material that settles at the interface between said first level and said second level of said gradient, said material containing dense microspheres; and (D) enriching said material as to the concentration of said dense microspheres to obtain a microsphere-enriched material.

6. A product according to claim 5, wherein said step of enriching said material comprises subjecting said material to a third centrifugation, at about 10,000 rpm for about 7 minutes, to obtain a microsphere-enriched sediment.

7. A composition that is the product of a process comprising the steps of (A) subjecting homogenized mammalian brain to a first centrifugation, at about 200 rpm for about 10 minutes, to obtain a sediment; (B) separating said sediment across a sucrose gradient via a second centrifugation at about 26,000 rpm for about 30 minutes, said sucrose gradient comprising a variation in sucrose concentration between at least a first level of about 52% sucrose content and a second level of about 56.7% sucrose content and further comprising an interface between said first level and said second level; (C) isolating material that settles at the interface between said first level and said second level of said gradient, said material containing dense microspheres; (D) enriching said material as to the concentration of said dense microspheres by subjecting said material to a third centrifugation, at about 10,000 rpm for about 7 minutes, to obtain a microsphere-enriched sediment; and (E) separating said microsphere-enriched sediment over a density gradient and obtaining a microsphere-enriched fraction of said density gradient.

* * * * *

UNITED STATES PATENT AND TRADEMARK OFFICE
CERTIFICATE OF CORRECTION

PATENT NO. : 4,816,416

DATED : March 28, 1989

INVENTOR(S) : Paul AVERBACK

It is certified that error appears in the above-identified patent and that said Letters Patent is hereby corrected as shown below:

IN THE TITLE: [54] Correct spelling of "ALZHEIMER'S".

COVER PAGE: 2nd col., line 4, correct spelling of "Plaque";
                line 8, change "Spheres" to --spheres--;
                line 12, correct spelling of "Plaque";
                line 13, change "Lejournal" to --le Journal--;
                line 16, correct spelling of "Plaques"; and
                line 19, correct the spelling of "Micospheres".

Col. 2, line 8, correct spelling of "NEUTOPATHOLOGY".

Col. 4, line 63, change "DSM" to --DMS--.

Col. 5, line 18, change "nd" to --and--.

Col. 6, line 55, change "an" to --and--; and
      line 61, change "tcm" to --5cm--.

UNITED STATES PATENT AND TRADEMARK OFFICE
CERTIFICATE OF CORRECTION

PATENT NO. : 4,816,416

DATED : March 28, 1989

INVENTOR(S) : Paul AVERBACK

It is certified that error appears in the above-identified patent and that said Letters Patent is hereby corrected as shown below:

Col. 7, line 42, change "the" to --The--;

line 52, delete "are"; and line 50, after "followed" insert --in--.

Signed and Sealed this

Tenth Day of July, 1990

*Attest:*

HARRY F. MANBECK, JR.

*Attesting Officer*   *Commissioner of Patents and Trademarks*